United States Patent
Schmaltz et al.

(10) Patent No.: US 6,464,704 B2
(45) Date of Patent: Oct. 15, 2002

(54) BIPOLAR ELECTROSURGICAL INSTRUMENT WITH REPLACEABLE ELECTRODES

(75) Inventors: Dale Francis Schmaltz, Fort Collins, CO (US); Robert Luzzi, Boulder, CO (US); David Nichols Heard, Boulder, CO (US); Steven Paul Buysee, Longmont, CO (US); Kate Ryland Lawes, Boulder, CO (US); Daniel Lee Trimberger, II, Greeley, CO (US); Mathew Erle Mitchell, Boulder, CO (US); Jenifer Serafin Kennedy, Boulder, CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/885,673

(22) Filed: Jun. 20, 2001

(65) Prior Publication Data
US 2001/0037110 A1 Nov. 1, 2001

Related U.S. Application Data

(63) Continuation of application No. 09/387,883, filed on Sep. 1, 1999, now abandoned, which is a continuation of application No. 08/968,496, filed on Nov. 12, 1997, now Pat. No. 6,050,996.

(51) Int. Cl.[7] .............................................. A61B 18/18
(52) U.S. Cl. .......................................... 606/51; 606/50
(58) Field of Search ............................. 606/51, 52, 41, 606/45, 48–50, 205, 208

(56) References Cited

U.S. PATENT DOCUMENTS

| | | |
|---|---|---|
| 5,007,908 A | 4/1991 | Rydell |
| 5,197,964 A | 3/1993 | Parins |
| 5,215,101 A | 6/1993 | Jacobs et al. |
| 5,282,799 A | 2/1994 | Rydell |
| 5,290,286 A | 3/1994 | Parins |
| 5,318,589 A | 6/1994 | Lichtman |
| 5,334,215 A | 8/1994 | Chen |
| 5,342,381 A | 8/1994 | Tidemand |
| 5,411,519 A | 5/1995 | Tovey et al. |
| 5,443,480 A | 8/1995 | Jacobs et al. |
| 5,445,638 A | 8/1995 | Rydell et al. |
| 5,514,134 A | 5/1996 | Rydell et al. |
| 5,540,685 A | 7/1996 | Parins et al. |
| 5,603,711 A | 2/1997 | Parins et al. |
| 5,707,369 A | 1/1998 | Vaitekunas et al. |
| 5,743,906 A | 4/1998 | Parins et al. |
| 5,766,170 A | 6/1998 | Eggers |

(List continued on next page.)

FOREIGN PATENT DOCUMENTS

| | | |
|---|---|---|
| CA | 2104423 | 2/1994 |
| WO | WO 99/12488 | 3/1999 |

Primary Examiner—Michael Peffley

(57) ABSTRACT

A bipolar electrosurgical instrument for vessel sealing comprises first and second members connected by a pivot. A pair of jaws have opposable seal surfaces that are designed to grasp vascular tissue and conduct bipolar electrosurgical current therethrough. Electrodes on the jaws, including the seal surfaces, are removable and disposable. The jaws of the instrument have mechanical interfaces designed to accept replacement electrodes. The instrument further comprises interlocking ratchets designed to hold a constant closure force between the seal surfaces. Wires extend from the electrodes along one of the members and are connectable to an electrosurgical generator.

8 Claims, 5 Drawing Sheets

U.S. PATENT DOCUMENTS

| | | |
|---|---|---|
| 5,800,449 A | 9/1998 | Wales |
| 5,814,043 A | 9/1998 | Shapeton |
| 5,827,279 A | 10/1998 | Hughett et al. |
| 5,843,080 A | 12/1998 | Fleenor et al. |
| 5,891,141 A | 4/1999 | Rydell |
| 5,891,142 A | 4/1999 | Eggers et al. |
| 5,902,301 A | 5/1999 | Olig |
| 5,908,420 A | 6/1999 | Parins et al. |
| 5,913,874 A | 6/1999 | Berns et al. |
| 5,921,984 A | 7/1999 | Sutcu et al. |
| 5,935,126 A | 8/1999 | Riza |
| 5,954,720 A | 9/1999 | Wilson et al. |
| 5,976,132 A | 11/1999 | Morris |
| 6,004,335 A | 12/1999 | Vaitekunas et al. |
| 6,039,733 A | 3/2000 | Buysse et al. |
| 6,053,914 A | 4/2000 | Eggers et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,099,550 A | 8/2000 | Yoon |
| 6,110,171 A | 8/2000 | Rydell |
| 6,113,596 A | 9/2000 | Hooven et al. |
| 6,113,598 A | 9/2000 | Baker |
| 6,126,658 A | 10/2000 | Baker |
| 6,152,923 A | 11/2000 | Ryan |
| 6,174,309 B1 | 1/2001 | Wrublewski et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,206,877 B1 | 3/2001 | Kese et al. |

BIPOLAR ELECTROSURGICAL INSTRUMENT WITH REPLACEABLE ELECTRODES

CROSS REFERENCE TO RELATED APPLICATION

This application is a continuation of U.S. application Ser. No. 09/387,883 filed on Sep. 1, 1999 now abandoned, which is a continuation of U.S. application Ser. No. 08/968,496 filed on Nov. 12, 1997 now U.S. Pat. No. 6,080,996 both of which are hereby incorporated by reference in their entirety.

FIELD OF THE INVENTION

This invention relates to a bipolar electrosurgical instrument, and more particularly to a bipolar electrosurgical instrument having replaceable electrodes for sealing vessels and vascular tissue.

BACKGROUND OF THE DISCLOSURE

A hemostat is commonly used in surgical procedures to grasp, dissect and clamp tissue. It is typically a simple pliers-like tool that uses mechanical action between its jaws to constrict vessels without cutting them. It is also typical to have a interlocking ratchet between the handles so that the device can be clamped and locked in place.

Many hemostats are used in a typical open-surgical procedure. Once vascular tissue has been clamped with a hemostat, it is common for a surgeon to tie a suture around the tissue to close it off permanently prior to removing the hemostat. Several hemostats may be left in the surgical field until the surgeon has the opportunity to tie a suture around each section of clamped tissue.

Neurosurgeons have used bipolar instruments to coagulate vessels in the brain that are smaller than two millimeters in diameter. These bipolar instruments are typically tweezers-like devices with two arms that can be deflected toward each other to grasp tissue. However, it has been found that these instruments are not capable of sealing blood vessels with diameters larger than about two millimeters. There has been a long-felt need for an easy way to seal larger vessels and vascular tissue bundles without the need for sutures.

It is thought that the process of coagulating small vessels is fundamentally different then vessel sealing. Coagulation is defined as a process of desiccating tissue wherein the tissue cells are ruptured and dried. Vessel sealing is defined as the process of liquefing the collagen in the tissue so that it crosslinks and reforms into a fused mass. Thus, coagulation of small vessels is sufficient to permanently close them. Larger vessels need to be sealed to assure permanent closure.

A number of bipolar electrosurgical forceps and clamps are known in the field. However, these instruments are not designed to apply the correct pressure to a blood vessel to achieve a lasting seal. All of these instrument also suffer from the drawback that they do not combine the simplicity and familiarity of a hemostat with a bipolar electrosurgical circuit.

An example of a bipolar electrosurgical power curve for vessel sealing is disclosed in a U.S. Patent application entitled, "Energy Delivery System for Vessel Sealing," Ser. No. 08/530,495, filed Sep. 19, 1995, and is hereby incorporated by reference and made a part of this disclosure.

A U.S. Patent application entitled, "Vascular Tissue Sealing Pressure Control and Method," Ser. No. 08/530,450, filed on Sep. 19, 1995, discloses another surgical tool for sealing vessels, and is hereby incorporated by reference and made a part of this disclosure.

U.S. Pat. No. 371,664 discloses a pair of electric forceps with positive and negative electric poles located on the jaws.

U.S. Pat. No. 728,883 discloses an electrothermic instrument in which electricity is used to heat one of the jaws of the instrument.

U.S. Pat. No. 1,586,645 disclose; a bipolar instrument for coagulating tissue.

U.S. Pat. No. 2,002,594 discloses a bipolar laparoscopic instrument for treating tissue, whereby coagulation and cutting of tissue can be performed with the same instrument.

U.S. Pat. No. 2,176,479 discloses an instrument for finding and removing metal particles. The jaws of the instrument are designed to complete an electrical circuit when conductive material is placed therebetween. An insulated pivot and an insulated ratchet are used to prevent a short circuit.

U.S. Pat. No. 3,651,811 discloses a bipolar electrosurgical instrument for cutting and coagulating tissue.

U.S. Pat. No. 4,005,714 discloses bipolar coagulation forceps with jaws that open and close by way of an actuating sleeve.

U.S. Pat. Nos. 4,370,980 and 5,116,332 disclose an electrocautery hemostats wherein the hemostatic clamping function and the electrocautery function may be accomplished with a single instrument. Monopolar electrosurgical designs are shown and described.

U.S. Pat. No. 4,552,143 discloses a family of removable switch electrocautery instruments, including an electrocautery hemostat. Monopolar electrosurgical designs are shown and described.

U.S. Pat. No. 5,026,370 discloses an electrocautery forceps instrument having an enclosed electrical switching mechanism. Monopolar electrosurgical designs are shown and described.

U.S. Pat. No. 5,443,463 discloses coagulating forceps having a plurality of electrodes.

U.S. Pat. No. 5,484,436 discloses bipolar electrosurgical instruments for simultaneously cutting and coagulating tissue.

The article, "The Mechanism of Blood Vessel Closure by High Frequency Electrocoagulation" discloses experiments upon the blood vessels of dogs. The sentence starting on the last line of page 823 describes "an electrode forceps, each of the blades being insulated form the other and each connected to a terminal of the high frequency generator."

The article, "Studies on coagulation and development of an automatic computerized bipolar coagulator" discloses on page 150 that, "It was not possible to coagulate safely arteries with a diameter larger than 2 to 2.5 mm." On page 151, line 5, it is noted that "Veins can be coagulated safely up to a diameter of 3 to 4 mm."

Russian Patent 401,367, translation enclosed, discloses a bipolar instrument with a linkage that brings the working jaws together in a parallel manner.

Prior disclosures have not provided a design for a bipolar electrosurgical instrument with removable electrodes capable of conveniently applying a constant pressure, from a calibrated spring-loaded source held by a ratchet, that is sufficient to seal vessels and vascular tissue.

SUMMARY OF THE INVENTION

It is the general object of this invention to provide a bipolar electrosurgical instrument or sealing vessels and vascular tissue. The instrument is designed to grasp and clamp vessels or vascular tissue between its jaws. The jaws have removable electrodes that are electrically connected to an electrosurgical generator. Electrosurgical current flows through the clamped tissue between the electrodes. The instrument is bipolar because electrosurgical current flows from one electrode, through the tissue, to another electrode, and both electrodes are located on the instrument. In contrast, a monopolar instrument requires a separate electrode (sometimes called an "neutral electrode") that is located remote from the instrument.

One of the advantages of the instrument is that vessels and vascular tissue can be sealed without the use of sutures, staples, or other material that is foreign to the tissue.

Another advantage of the instrument is that the removable electrodes provide safety against electrical shocks and burns. Electrically insulative materials, such as plastics, can be damaged or compromised by repeated sterilization cycles. It is also possible for electrical insulation to be cut or nicked by sharp surgical tools. Removable electrodes provide a safety advantage because they can be replaced prior to each procedure. The electrodes can also be replaced at any time if the surgeon suspects an electrical insulation failure. This advantage is particularly important for vessel sealing instruments because currents up to 4 amperes may be used.

The present invention is a bipolar electrosurgical instrument comprising first and second members having first and second jaws near a distal end, and having first and second handles near a proximal end. A pivot joint connects the first and second members to allow for arcuate motion of the first and second jaws toward each other. First and second mechanical interfaces are located respectively on the first and second jaws. The first and second mechanical interfaces are preferably shaped to removably mate with first and second electrodes. The mating portion of the electrodes are made from an insulative material to prevent electrical conduction to the members. Seal surfaces on the opposable electrodes are preferably designed to clamp vessels and vascular tissue and conduct electrosurgical current therethrough in a bipolar circuit. First and second interlocking ratchets are located on the proximal end of the members to provide a constant closure force between the seal surfaces.

DETAILED DESCRIPTION OF THE INVENTION

Figure 1:
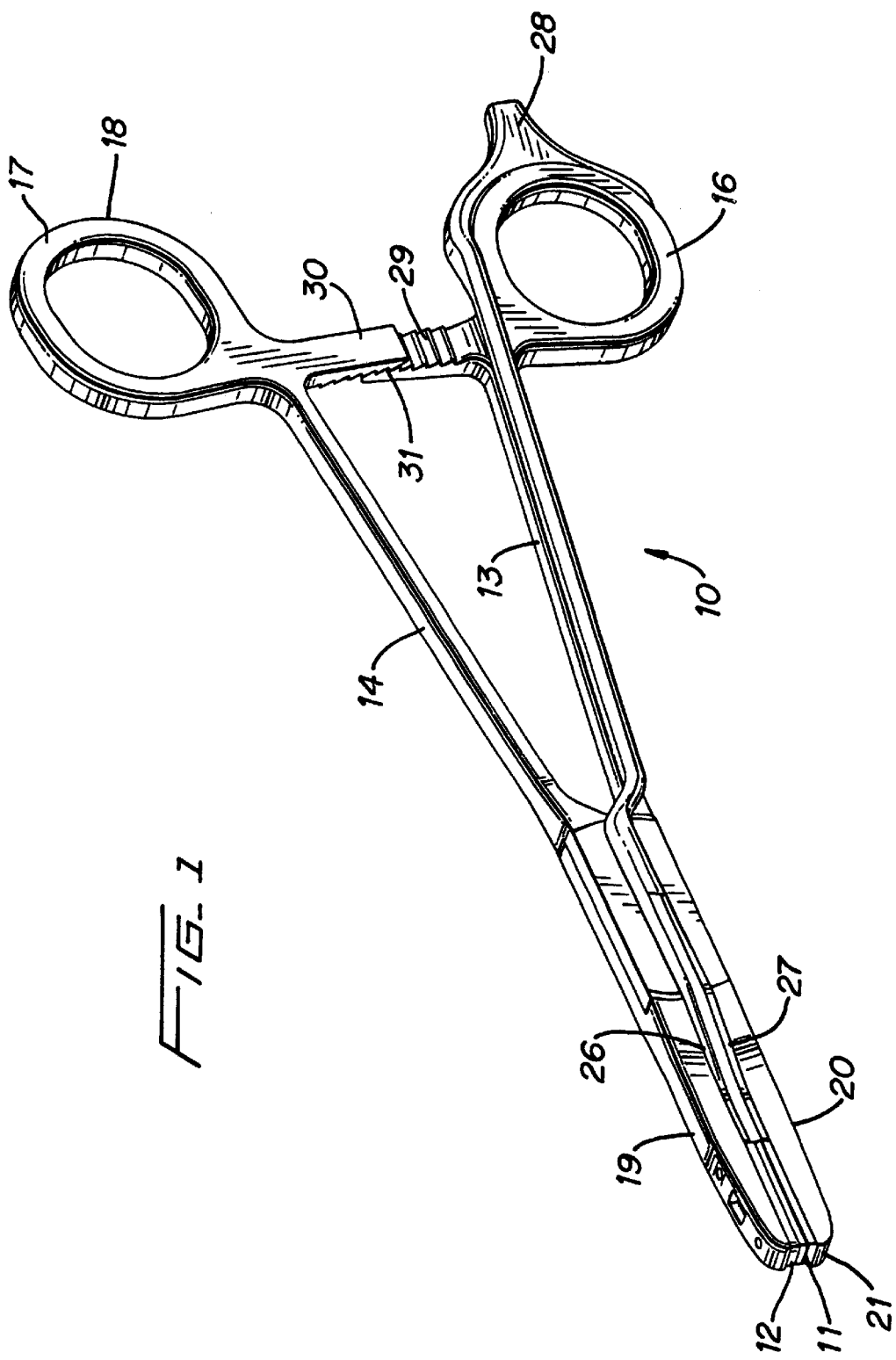
FIG. 1 is a perspective view of a bipolar electrosurgical instrument showing the electrodes mated together in parallel opposition.
Figure 2:
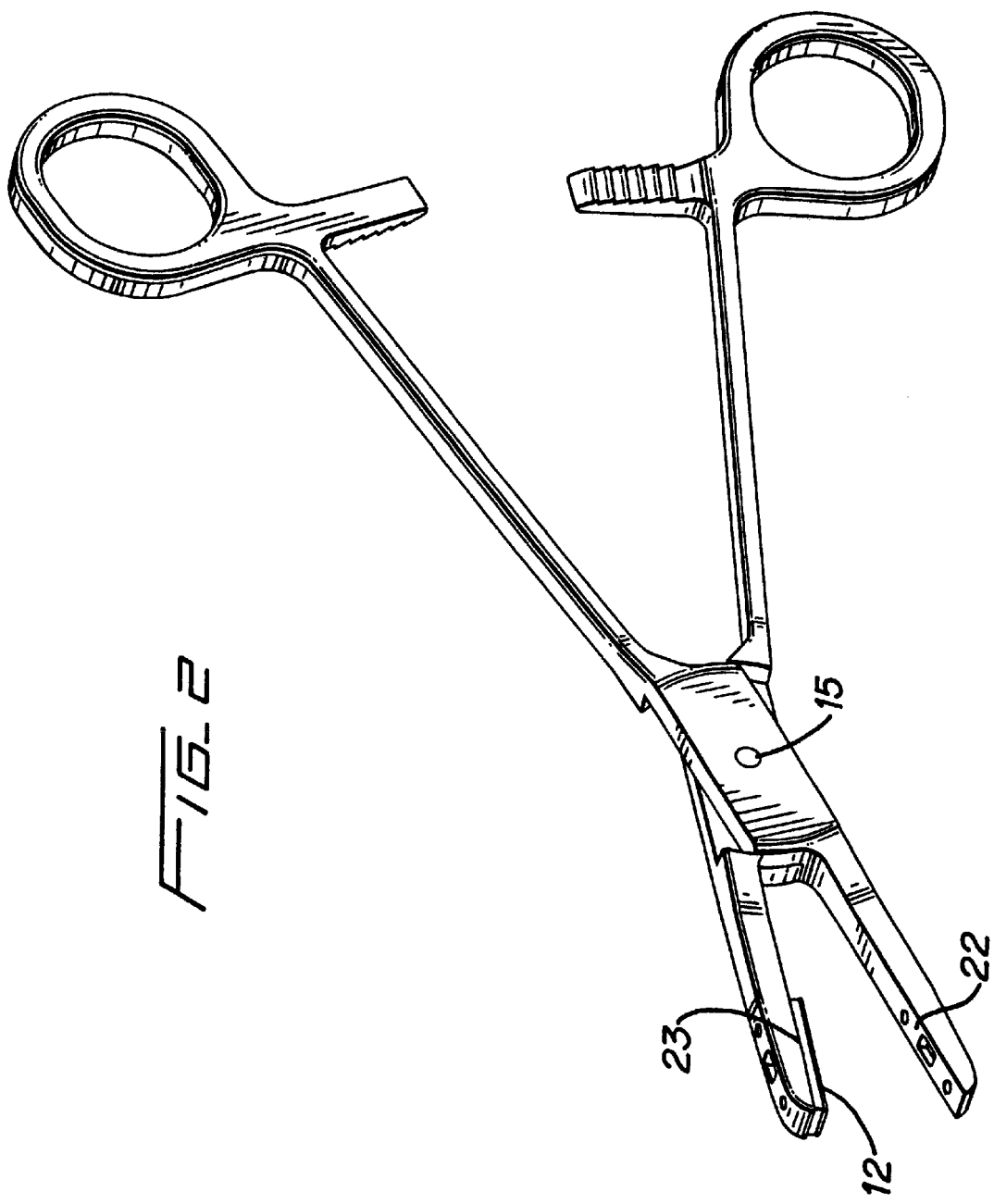
FIG. 2 is a perspective view of a bipolar electrosurgical instrument, showing one electrode removed with the socket in view, and one electrode in place.
Figure 4:
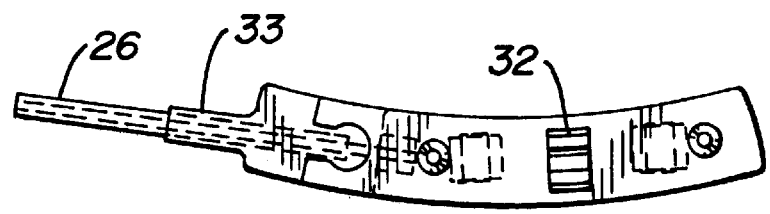
FIG. 4 is a bottom view of a replaceable electrode showing the electrically insulative substrate with a portion of a wire attached.

Referring to FIG. 1, a bipolar electrosurgical instrument 10 is shown with replaceable electrodes 11 and 12 for sealing vessels and vascular bundles. The instrument 10 comprises a first member 13 and a second member 14 that are connected at a pivot joint 15. Handles 16 and 17 are located generally at the proximal end 18. Jaws 19 and 20 are located generally at the distal end 21. Sockets 22 and 23 are located on the jaws 19 and 20. The sockets 22 and 23 each preferably comprise several features, as shown in FIG. 2 at the location where the electrode 11 is removed. In one embodiment, shown in FIG. 1, the jaws 19 and 20 are straight. In alternative embodiments, the jaws 19 and 20 may be curved to accept curved electrodes 11 and 12, as shown in FIG. 4.

Figure 3:
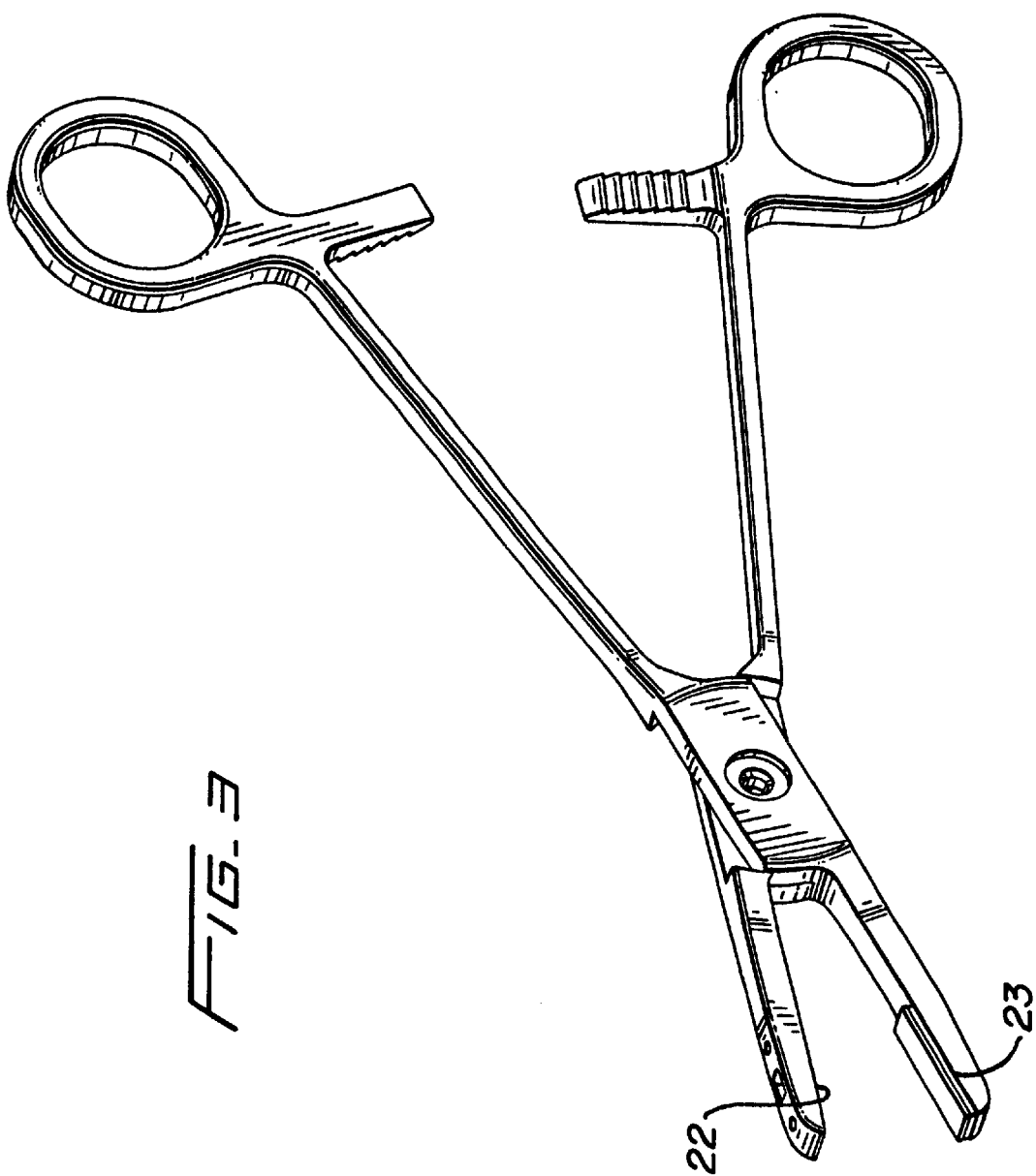
FIG. 3 is a perspective view of a bipolar electrosurgical instrument, showing one electrode in place and one electrode removed.

The first and second electrodes 11 and 12 are removably mounted respectively in the first and second sockets 22 and 23. While the term socket is used herein, it will be understood that either a male or female mechanical interface may be used on the jaws 19 and 20, with a mating mechanical interface on the electrodes 11 and 12. In FIG. 2, one of the sockets 22 is shown with the electrode 11 removed. FIG. 3 shows the socket 23 with an electrode 12 mated therein.

Figure 5:
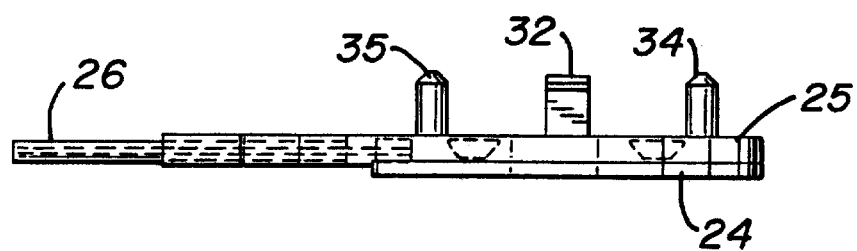
FIG. 5 is a side view of FIG. 4.
Figure 7:
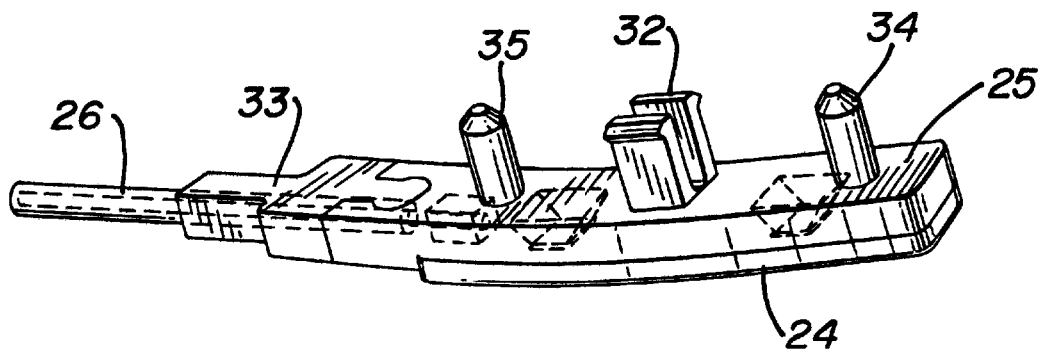
FIG. 7 is a perspective view of a replaceable electrode.

Each of the first and second electrodes 11 and 12 has an electrically conductive seal surface 24 and an electrically insulative substrate 25, as shown in FIGS. 5 and 7. Each substrate 25 is shaped to engage one of the first or second sockets 22 or 23 with mating features that fit removably within the sockets 22 or 23. In the preferred embodiment, the seal surfaces 24 are relatively flat to avoid current concentrations at sharp edges, and to avoid arcing between high points.

First and second wires 26 and 27 are connected to the first and second electrodes 11 and 12, respectively, as shown in FIGS. 1, 4, 5, and 7. In the preferred embodiment, the wires 26 and 27 are bundled together along one of the members 13 or 14 from the proximal end 18 to the pivot 15. Near the pivot 15, the wires 26 and 27 are separated and connected each to its respective electrode 11 or 12. This arrangement of wires 26 and 27 is designed to be convenient for the surgeon so that there is little interference with the manipulation of the instrument 10. The wires 26 and 27 are preferably terminated in a connector 2 near the proximal end 18, although in another embodiment the wires 26 and 27 may extend all the way to an electrosurgical generator. In an alternative embodiment, the wires 26 and 27 each extend along a separate handle 16 or 17.

First and second ratchets, 29 and 30, are located on the members 13 and 14 near the handles 16 and 17, as shown in FIGS. 1, 2, and 3. The ratchets 29 and 30 interlock in at least one position, shown in FIG. 1 at 31. In the preferred embodiment, there are several interlocking positions. The ratchet position 31 holds strain energy in the first and second members 13 and 14 to force the electrodes 11 and 12 against each other in opposition.

Each member 13 and 14 is preferably designed to deflect in a shank portion, defined as the section between the pivot 15 and the location of the ratchet. The jaws 19 and 20 are preferably more rigid than the shank portions. A lateral deflection of the shank portion causes strain due to bending that behaves like a spring. The strain energy that is stored in the shank provides a constant closure force between the electrodes 11 and 12. A design without a ratchet requires the surgeon to hold the electrodes together by applying a constant squeeze to the handles. It has been found through experimentation that a constant force throughout the sealing process will yield a more predictable surgical outcome. It is difficult to hold a constant force by hand, therefore a ratchet in combination with a deflectable shank mill provide a better surgical outcome.

Figure 8:
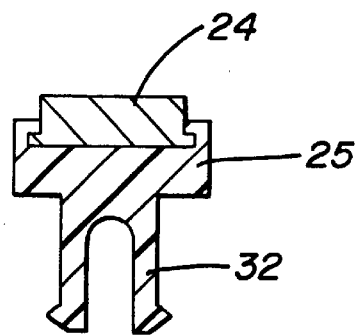
FIG. 8 is side view of an electrode showing a forked snapfit extension.

The electrically insulative substrate 25 on each of the electrodes 11 and 12 is preferably made from an injection moldable plastic. The substrate 25 is preferably overmolded to capture the electrically conductive seal surface 24, as shown in FIG. 8. Wires 26 and 27 are electrically connected to the seal surface 24 of each electrode 11 or 12. There is preferably a strain relief feature 33 on the electrodes 11 and 12, as shown in FIGS. 4 and 7.

Figure 6:
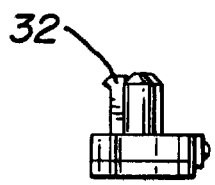
FIG. 6 is a detail view of a forked snapfit extension.
Figure 9:
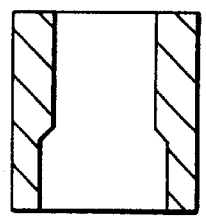
FIG. 9 is a partial side view of a portion of a socket designed to receive the snapfit extension.
Figure 10:
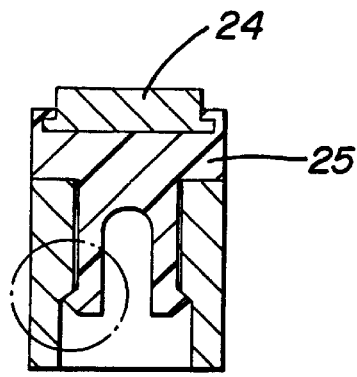
FIG. 10 is a partial side view of an electrode seated in a socket.
Figure 11:
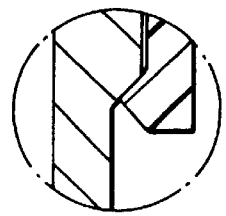
FIG. 11 is an enlarged view of a portion of a snap-fit extension seated in a socket.

The substrate 25 preferably comprises a forked snap fit extension 32 as shown in detail in FIG. 6. Each jaw 19 and 20 has a socket 22 and 23 that comprises a recess 34, shown in FIG. 9, shaped to capture the forked snap fit extension 32. One of the advantages of this design is that manufacturing tolerances can be accommodated by the snap fit as shown in FIG. 11. The preferred embodiment also comprises a pair of alignment pins 37 and 35 that fit into the sockets 22 and 23.

In the preferred embodiment, the instrument 10 is designed so that the electrodes 11 and 12 meet in parallel opposition. Thus, opposing seal surfaces 24 meet each other in the same plane, as shown in FIG. 1. In an alternative embodiment, the seal surfaces can be slightly biased to meet each other at the distal end, and further closure force at the handles will cause the seal surface 24 on each electrode 11 and 12 to deflect together in the same plane. In certain embodiments, there may be a stop to create a fixed gap, preferably about 0.3 millimeters, to prevent shorting of the electrodes. Other embodiments have an insulative element on each jaw that opposes the conductive seat surface 24 on the opposing jaw, such that the instrument 10 does not short circuit when the jaws 19 and 20 are closed together.

It has been determined experimentally that the closure force between the seal surfaces 24 is preferably sufficient to overcome a tendency of the tissue to expand during heating. The sealed tissue thickness must be less than the initial tissue thickness, under pressure, in order to create a fused vessel wall. The amount of pressure required depends on the type of tissue, and the dimensions of the seal surfaces 24, and the size of the tissue that is grasped with the instrument 10. The pressure is expressed herein as a formula depending on the width of the seal surface and the closure force between the seal surfaces.

For an instrument designed for abdominal vessels and vascular bundles, each seal surface 24 has a width that is preferably in the range of 2 to 5 millimeters, and a length in the range of 10 to 30 millimeters. For abdominal vessels and vascular bundles, experimental results indicate that good vessel sealing performance can be achieved when the instrument 10 is calibrated to have at least one ratchet position 31 set such that the closure force (in grams) divided by the width of the seed surface (in millimeters) is in the range of 400 to 650, and most preferably 525. For example, an instrument with a seal surface width of 4 millimeters would preferably have a closure force of 2100 grams.

For an instrument designed for thick connective tissues and ligaments, particularly a hysterectomy style Heaney device, the closure force (in grams) divided by the width of the seal surface (in millimeters) is in the range of 1000 to 2000. Such an instrument would also preferably have a cross hatched or knurled seal surfaces 24 to improve grasping capability, but the height of the roughness features should be minimized to avoid arcing.

While a particular preferred embodiment has been illustrated and deck the scope of protection sought is in the claims that follow.

What is claimed is:

1. A bipolar electrosurgical instrument comprising:

a pair of first and second members each having a jaw member extending from a distal end thereof and a handle disposed at a proximal end thereof for effecting movement of the jaw members relative to one another;

at least one electrode having an electrically conductive seal surface and an insulating substrate, the insulative substrate being overmolded to capture the electrically conductive seal surface; and at least one mechanical interface extending from the insulative substrate which engages a corresponding mechanical interface disposed on one of the jaw members to secure the electrode to the jaw member.

2. A bipolar electrosurgical instrument according to claim 1 wherein the insulative substrate includes a forked extension which engages a corresponding recess in one of the jaw members to secure the electrode to the jaw member.

3. A bipolar electrosurgical instrument according to claim 2 wherein the recess is dimensioned to engage the forked extension.

4. A bipolar electrosurgical instrument according to claim 1 wherein the insulative substrate further includes a n alignment pin which engages a corresponding socket disposed within one of the jaw members.

5. A bipolar electrosurgical instrument according to claim 1 wherein the electrically conductive seal surface of the electrode is generally flat to limit current concentration along an edge of the electrode.

6. A bipolar electrosurgical instrument according to claim 1 wherein the electrode is removably mounted to at least one of the jaw members.

7. A bipolar electrosurgical instrument according to claim 1 including a pair of electrodes each removably engage a corresponding jaw members, the pair of electrodes including first and second wires which are bundled along at least one of the first and second members.

8. A bipolar electrosurgical instrument according to claim 1 wherein the electrode includes a strain relief member.

* * * * *